United States Patent
Kramann

(10) Patent No.: US 9,320,629 B2
(45) Date of Patent: Apr. 26, 2016

(54) STENT FOR TEMPORARY FITTING IN A BODY CAVITY

(75) Inventor: Bernhard Kramann, Homburg (DE)

(73) Assignee: PFM MEDICAL AG, Cologne (DE)

( * ) Notice: Subject to any disclaimer, the term of this patent is extended or adjusted under 35 U.S.C. 154(b) by 1512 days.

(21) Appl. No.: 12/083,804

(22) PCT Filed: Oct. 19, 2006

(86) PCT No.: PCT/DE2006/001847
§ 371 (c)(1),
(2), (4) Date: Nov. 30, 2011

(87) PCT Pub. No.: WO2007/045229
PCT Pub. Date: Apr. 26, 2007

(65) Prior Publication Data
US 2012/0095541 A1  Apr. 19, 2012

(30) Foreign Application Priority Data
Oct. 20, 2005  (DE) .......................... 10 2005 050 386

(51) Int. Cl.
*A61F 2/06*  (2013.01)
*A61F 2/95*  (2013.01)
*A61F 2/90*  (2013.01)

(52) U.S. Cl.
CPC ... *A61F 2/95* (2013.01); *A61F 2/90* (2013.01); *A61F 2002/9511* (2013.01); *A61F 2002/9528* (2013.01)

(58) Field of Classification Search
CPC ..... A61F 2/90; A61F 2/95; A61F 2002/9528; A61F 2002/9511

USPC .......... 623/1.11, 1.15, 1.16, 1.17, 1.18, 1.19; 606/194, 198
See application file for complete search history.

(56) References Cited

U.S. PATENT DOCUMENTS

| 4,580,568 | A | * | 4/1986 | Gianturco ..................... 606/198 |
| 4,950,258 | A | | 8/1990 | Kawai et al. |
| 5,035,706 | A | * | 7/1991 | Giantureo et al. ............ 606/198 |
| 5,643,309 | A | | 7/1997 | Myler et al. |
| 5,800,525 | A | * | 9/1998 | Bachinski et al. ............. 623/1.1 |
| 6,569,191 | B1 | | 5/2003 | Hogan |
| 7,252,680 | B2 | * | 8/2007 | Freitag ......................... 623/1.12 |

(Continued)

FOREIGN PATENT DOCUMENTS

| DE | 198 28 415 A1 | 1/1999 |
| DE | 101 18 944 A1 | 10/2002 |

(Continued)

OTHER PUBLICATIONS

Rabkin, D.J., Retrievable Intravascular Implants: A New Approach in the Management of Cardiovascular Disorders, Presentation No. P82, Poster Board No. 82.

*Primary Examiner* — Katrina Stransky
(74) *Attorney, Agent, or Firm* — Grossman, Tucker, Perreault & Pfleger, PLLC

(57) ABSTRACT

A stent for positioning in a body lumen having a cylindrical shape extending along a longitudinal axis surrounded by a stent wall which defines a diameter of an axial passage communicating with openings on two opposite ends of the stent. The wall is configured so as to be elastic under tension whereupon an exertion of a tensile force acting on one of the ends of the stent in a longitudinal direction decreases the diameter of the stent, such that the stent may be removed.

9 Claims, 3 Drawing Sheets

(56) References Cited

U.S. PATENT DOCUMENTS

2002/0188344 A1* 12/2002 Bolea et al. .................. 623/1.11
2003/0149475 A1* 8/2003 Hyodoh et al. ............... 623/1.19
2004/0116996 A1* 6/2004 Freitag ......................... 623/1.11
2006/0036308 A1* 2/2006 Goshgarian .................. 623/1.11

FOREIGN PATENT DOCUMENTS

| EP | 0 423 916 A1 | 4/1991 |
| EP | 1 033 145 A1 | 9/2000 |
| WO | PCT/GB00/02735 | 1/2001 |
| WO | PCT/US2004/016288 | 12/2004 |

* cited by examiner

STENT FOR TEMPORARY FITTING IN A BODY CAVITY

The present invention relates to a stent for temporary implanting in a body lumen, as disclosed in the preamble of claim 1, and a kit of parts that contains such a stent.

To date stents have been used to treat the narrowing of body lumens—so-called stenosis. Such a stenosis can develop, for example, in blood vessels, in particular the arteries, but also in other body lumens, such as the bile duct. Stenosis is often the result of plaque, building up on the inner wall of the vessel, and may lead to a dangerous vascular occlusion. Such a vascular occlusion may lead to an infarction, which may have, inter alia, serious consequences, such as cardiac arrest, a stroke or the loss of limbs.

In order to prevent the collapse and/or occlusion of a vessel, interventional medicine uses a balloon catheter or stent that is inserted into the impaired body lumen.

In the former case the balloon is inflated in situ, thus dilating and enlarging the blood vessel (balloon angioplasty). In the best case scenario this procedure remedies the stenosis; and the vessel becomes passable again.

In the second case a stent—thus, typically a tubular, wire mesh-type structure—is inserted into the vessel and positioned in situ in the compressed state by means of a catheter and is then dilated. This procedure can be carried out with a balloon catheter or with a so-called shape memory material, which returns in situ to its originally imprinted shape due to a temperature impulse. On the one hand, the stent may help to expand the stenosis and, on the other hand, may supplement the expanded vessel in order to prevent restenosing.

Balloon angioplasty has proven to be effective in remedying stenosis in many body lumens. In many cases the result is a permanent expansion of the vessel at a relatively low rate of recurrence.

However, in some areas of the body, such as on the periphery, and in this case especially in the leg vessels, a significantly higher rate of recurrence following balloon angioplasty has been observed. Owing to the biomechanical conditions prevailing in these areas, extreme overdilation is often necessary in order to expand to an adequately sufficient extent the existing stenosis. However, the result of this overdilation is often a dissection of the wall of the respective blood vessel. That is, the result is often a detachment or delamination of the individual layers of the vessel wall. In especially sensitive vessels, a dissection may occur even without an extreme overdilation. For example, it must be pointed out that after balloon angioplasty, which caused an extreme overdilation of the blood vessel, the inner lining (intima) of the vessel may delaminate or detach over longer sections of those layers of the wall of the blood vessel that are located more towards the periphery (media), thus under some circumstances displacing the vascular lumen; and this in turn may lead to a vascular occlusion and/or an infarction.

In theory, this complication could be prevented by implanting, following balloon catheterization, a stent that can prevent the tunica intima from delaminating or, if the intima has already peeled off, that can prevent a displacement of the lumen of the blood vessel.

Under optimal circumstances the implanted stent may help the delaminated intima to re-adhere again to the vessel wall; and the aforementioned complication does not develop. Such a relamination often occurs in just a few days following positioning of the stent.

In many cases, such as in a coronary vessel, once the stent has been implanted, it can stay in that location and does not interfere with the normal physiological processes. In such cases, therefore, the said combination of balloon catheterization and implantation of a stent is easy to conceive. However, there are cases, in which it is indicated to remove the stent again from the vessel after a more or less long dwell time. Some examples are the aforementioned stents in leg arteries, which are exposed to high mechanical loads owing to the high mechanical loads, prevailing in the leg arteries, on account of the flexion of the leg and the continuous contraction and relaxation of the surrounding leg musculature. Eventually these high mechanical loads will lead to the destruction of the stent, which in turn may result in fatal consequences. Moreover, in this area, which is permanently in motion, a stent in a lumen may lead to constant irritation of the respective vessel wall, which in turn may result in restenosing of the vessel.

Therefore, in the medical literature the consensus is largely that stents should be implanted in the popliteal artery only in critical cases in order to save the leg from being amputated. However, stents in the popliteal artery and the femoral artery are subject to a high rate of restenosis and may impede or render impossible the surgical application of a bypass. In many professional circles, therefore, a stenosis in a peripheral vessel, in particular a leg artery, is regarded as untreatable with a stent. Therefore, in the USA peripheral stenosis is frequently an indication for an amputation.

In order to avoid this dramatic consequence, a stent would be desirable that is created in such a way that it can be implanted, for example, after balloon catheterization, in order to guarantee a relamination, thus re-adhesion, of the intima, and can be removed again from the vessel after a more or less long dwell time—but no later than at a point in time, when the stent has not yet become vascularized to the vessel wall.

However, the subsequent removal of the once implanted stent causes serious problems. When an expanded and/or dilated stent is pulled out of a body lumen, there is the risk that the surrounding tissue will be injured by abrasion, because the stent is too big and often exhibits sharp edges. A number of different methods and stents have been developed in order to solve this problem.

Therefore, there exists a method for removing stents made of shape memory materials. In this case a catheter is moved to a stent, which is positioned and expanded in a lumen, and the diameter of the stent is decreased by means of a temperature impulse (usually a cold stimulus in the range of about 0° C.), which causes the stent to return to a previously imprinted shape, so that this stent can be removed. Such methods are disclosed, for example, in the paper "Retrievable Intravascular Implants: A new approach in the management of cardiovascular disorders" by D. J. Rabkin, published in the conference volume of the annual meeting of the Cardiovascular and Interventional Radiological Society of Europe, Sep. 10-14, 2005, page 177.

However, such methods exhibit the drawback that recatheterization with the simultaneously dose of a temperature impulse is very expensive, and, in addition, entails risks for the patient, such as the risk of local congelation or similar injuries.

Other removable stents are made of a material, which over the course of time is degraded and decomposed by the body, so that the stent slowly dissolves. DE 10357744 (A1) describes such stents that are made of SMP materials (shape memory polymer). They are biodegradable and, moreover, exhibit shape memory properties. U.S. Pat. No. 4,950,258 describes similar stents that are made, for example, of lactide and/or glycolide.

U.S. Pat. No. 6,569,191 describes self-expanding stents made of biodegradable, woven threads. A plurality of bands, which are made of an elastic polymer that is also biodegradable, are affixed by adhesive to the outside of the stent. The bands may be made, for example, of a shape memory polymer, which is also based on lactic acid and/or glycolic acid. Furthermore, EP 1033145 describes the use of such additional materials comprising caprolacton, p-dioxanone or trimethylene carbonate.

However, the described materials exhibit to some extent a decomposition property that poses a problem. When these materials do not totally decompose, decomposition products may remain, which may ultimately lead to a new obstruction of the blood vessels or may cause other complications.

Therefore, the object of the present invention is to provide a removable stent that is easy to position and remove again and at the same time does not exhibit the aforementioned drawbacks. Hence, when the stent is removed, it shall not exert any tangential shearing forces on the vascular intima. Another object of the present invention is also to provide a method for removing such a stent.

Both of these objects are achieved by the features of the present independent claims.

These claims provide a stent, which is intended for positioning in a body lumen and which exhibits a cylindrical shape, running about a longitudinal axis, with a wall; two open ends, lying at opposite axial ends; a longitudinal extent and a diameter.

The stent, according to the invention, is characterized in that the wall is configured so as to be elastic under tension and is designed so that a tensile force, which acts on one of the ends of the stent in the longitudinal direction, decreases the diameter of the stent.

Such a behavior is already known from other structures having a cylindrical shape—for example, hoses made of thermoplastic material, or for example, also stockings.

The tensile force, exerted in the longitudinal direction, forces the wall components, which are arranged diagonally to the longitudinal and transverse direction of the structure, and the wall components, oriented in the transverse direction, to orient themselves more in the longitudinal direction. The transverse orientation of these components decreases, a state that leads to a decrease in the overall circumference and, thus, to a reduction in the diameter of the structure.

This behavior can be observed in not only elastic materials but also in non-elastic materials. In the latter case, however, the wall material has to exhibit individual components, which are oriented in different directions. In a practical embodiment the wall is configured as one piece. In this case, an especially suitable material for the wall is one made of a woven fabric, a knit fabric, a braided fabric, a mesh material or the like.

In this case it is especially preferred that at least one of the two ends of the stent exhibits terminal coupling devices, by means of which the end of the stent can be grasped; and a tensile force, acting in the longitudinal direction of the stent, may be fed into the stent. It is desirable for a plurality—preferably all—of the coupling devices to be held together, so that they may be jointly grasped; and the tensile force acts more or less uniformly on the ring-shaped end of the stent. The said coupling devices are, for example, loops, thickenings, eyes, hooks, plates or the like. They may contain preferably an x-ray opaque material, such as gold, platinum, silver, tantalum, a synthetic plastic material doped with barium sulfate or a synthetic plastic material doped with bismuth trioxide, in order to facilitate the localization of the stent and/or the coupling devices in the x-ray image.

In order to be able to feed a tensile force into the stent and not simply dislodge the stent from its position in the body lumen (a feature that is undesired because of the resulting risk of injury and complications), an abutment is necessary. First of all, this abutment holds the stent in its original position and secondly allows the exerted tensile force to act on the stent and in this way makes it possible to reduce the diameter.

To this end, one possibility does not require any additional measures with respect to devices. In this case it is assumed that a stent, which is positioned and expanded in a blood vessel, will adhere to the inner wall of the blood vessel. On the one hand, this adhesion is caused by a radially acting expansion force and/or by adhesive forces. Vascularization of the stent to the wall of the blood vessel is not desired. For this reason the stent remains only one to two days in the vessel so that it cannot become vascularized. The vascularization ensues relatively quickly. That is, just after four days it is coated with some type of endothelium and can no longer be removed without great effort.

If at this stage a tensile force is exerted on the stent from one side, the stent will then detach itself from the wall of the blood vessel on the side, from which the force is exerted, but it will continue to adhere to the side that is located further away. In any event this adhesion to the wall represents the requisite abutment that prevents the stent from being easily dislodged. As a result, the diameter of the stent is decreased in successive stages.

According to another embodiment, the stent is pulled into a catheter having an opening—a so-called delivery sheath. In this case the tensile force, which acts on the stent and which reduces its diameter, is also generated in that the end of the stent abuts the opening of the sheath which in this case acts as the abutment.

An especially preferred embodiment provides that the stent is designed in such a manner that owing to the decrease in diameter the stent can be retrieved from the body lumen.

In this case it is preferably provided that the tensile force, acting in the longitudinal direction of the stent, can be exerted on the stent by means of a catch device that is inserted into the lumen by means of a catheter. This catch device may be, for example, a wire loop, by means of which one terminal coupling device or a plurality of terminal coupling devices can be grasped.

In another especially preferred embodiment the wall of the stent is made of a woven wire, a knitted wire, and/or a braided wire or a wire mesh. Especially the latter may be, in particular, welded together. All of these types of walls exhibit wall components that on exertion of a tensile force are forced to orient themselves more in the longitudinal direction, a feature that leads to a decrease in the overall circumference and, thus, to a reduction in the diameter of the structure.

The material of the wall is preferably a material, selected from the group composed of stainless steel, synthetic plastic material, nickel-titanium alloy, copper-zinc-aluminum alloy or tungsten. In this case an especially preferred embodiment provides that the wall material exhibits shape memory properties and/or is biodegradable.

The shape memory materials are materials, the properties of which make it possible to impart to the stent an expanded shape prior to positioning, then to insert the stent in the compressed state into the body lumen and to expand the stent in said lumen either by means of a temperature controlling device, provided in the catheter, or by means of the body temperature of the patient.

Another preferred embodiment provides that the surface of the stent is processed, in particular, finished, smoothed. That is, the surface is smooth and flat and/or is polished or that its surface is provided with a coating for enhancing the slip properties. The latter may be, for example, silicones, parylenes or hydrogels.

All of these modifications raise the biocompatibility, in particular the hemocompatibility, of the stent, decrease the risk of thrombolization, and facilitate both the positioning and also the subsequent removal of the stent.

In particular, it may be provided that the stent and/or its wall material is/are loaded with therapeutic substances for supporting the healing processes or for suppressing restenosis or inflammation. For example, the stents are load with anti-inflammatory substances, antibiotics, antiviral substances, antimycotics, anti-coagulants, cytostatics, cell division inhibitors, immunosuppressive substances, growth factors or active substances for preventing restenosis.

In order to prevent and/or retard such a vascularization, it is preferred to provide the inventive stent with a coating that prevents vascularization or adhesion of the intima. Such coatings are well-known and are used in a number of biomedical devices, such as in heart valves, catheters, etc. The coating substances that are used usually exhibit a good barrier effect against water, inorganic and organic substances and are especially biocompatible. Such a coating is usually applied in a thickness ranging from 0.05 to 1 mm, in particular from 0.1 to 0.5 mm. The coating is usually carried out by means of chemical vapor deposition [CVD]. It is usually uniformly thick. Examples of such materials that are used for the coating are, in particular, organic polymers and preferably aromatic polymers, such as those composed of paraxylenes, which may or may not be substituted. Practical substituents are halogens, such as Cl. Such substances are commercially available under the tradenames "parylene C" or "parylene N."

In a corresponding embodiment the inventive stent is especially suitable for positioning in the knee artery, the femoral artery, dialysis shunts, the renal artery or a coronary vessel.

The stent, according to the invention, is used preferably in a "kit of parts," which exhibits, besides the stent, a catheter for positioning the stent in a body lumen, as well as a catch device, which can be inserted into the lumen by means of a catheter and which is intended for grasping one of the coupling devices of the stent and for feeding a tensile force into the stent. Other details of this kit may be inferred from the attached drawings.

In order to remove again a stent that has already been positioned in a body lumen, the following steps are taken.

First, a catch device is inserted into the body lumen by means of a catheter. Then, at least one terminal coupling device of the stent is grasped with the aid of the catch device. Preferably a plurality (expediently all) of the coupling devices are held jointly by the catch or gripping device. Then a tensile force, which acts on the end of the stent in the longitudinal direction, is exerted on the stent.

As described above, this is possible because the adhesion of the stent to the inner wall of the blood vessel acts as an abutment. As an alternative, the stent can be pulled into a catheter—a so-called delivery sheath—that in this case acts as an abutment.

In this case, owing to the exertion of the tensile force, acting on the end of the stent in the longitudinal direction, the diameter of the stent is decreased. The stent wall detaches itself from the inner wall of the vessel; and the stent, which has delaminated from the inner wall of the vessel and the diameter of which is decreased, may be pulled out of the body lumen and/or implanted again in another location.

Therefore, the inventive stent and/or the aforementioned method is/are especially suitable for the treatment of stenosis of the peripheral vessels, which were formerly expanded with a balloon catheter. The positioned stent may contribute to the re-vascularization of parts of the tunica intima that have been injured by the overdilation of the vessel and, thus, delaminated. Then the stent can be removed again before it itself becomes involved due to the ensuing physical stresses.

Hence, an instrumentarium is provided that renders, in particular, peripheral stenosis treatable and, in addition, may help to avoid the amputation that has been indicated to date in many cases.

The invention is explained below by means of an example with reference to the drawings. In this case embodiments are shown that are not intended to restrict in any way the field of protection sought with the presented claims.

Figure 1:
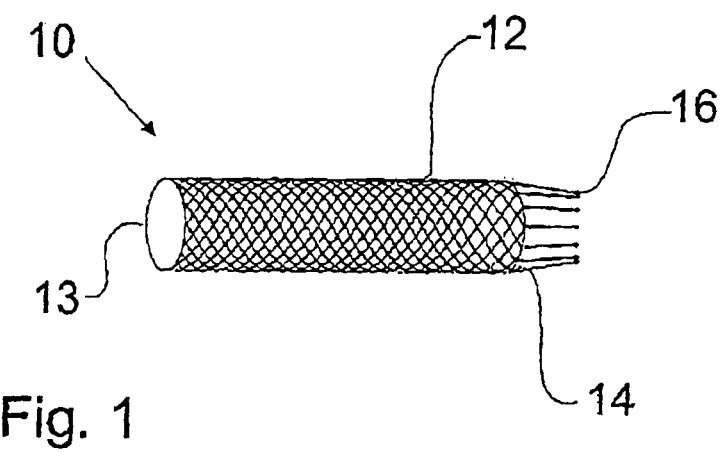
FIG. 1 is a schematic rendering of an inventive stent in the expanded form.
Figure 2:
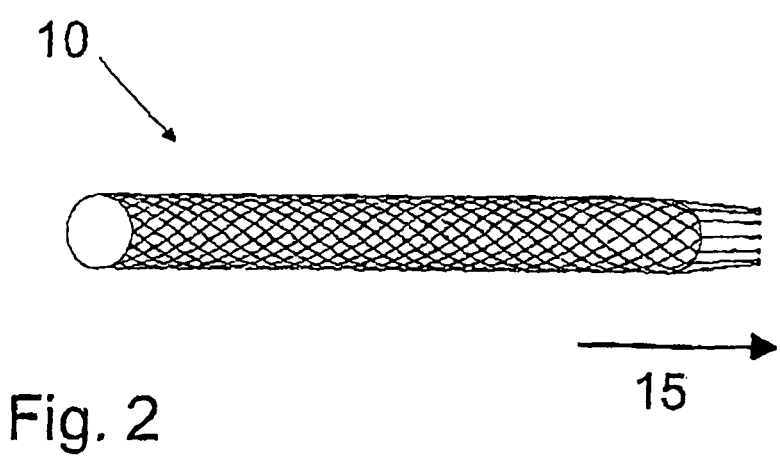
FIG. 2 depicts an inventive stent, the diameter of which has decreased owing to the action of a tensile force acting on one of the ends of the stent.

FIGS. 1 and 2 depict a stent 10 for positioning in a body lumen 11. Said stent exhibits a cylindrical shape, extending about a longitudinal axis, with a wall 12; two open ends 13, 14, which are located on opposite ends of the axis; a longitudinal extent as well as a diameter. In this case it must be pointed out that the lines that run in the shape of a ring and that run longitudinally describe only the surface of the stent and do not represent the lines of the weave.

The wall 12 is designed so as to be elastic under tension and is designed so that on exertion of a tensile force 15, which acts on one of the ends of the stent in the longitudinal direction, the diameter of the stent decreases.

In FIGS. 1 and 2 the wall 12 is depicted as a braided material comprising components arranged in the longitudinal direction and in the transverse direction (thus longitudinal and/or circumferential direction). In this case it must be pointed out that the lines, which run in the shape of a ring, and the lines that run longitudinally describe only the surface of the stent and do not represent the lines of the weave. However, in particular any type of woven wire, knitted wire and/or braided wire is possible in principle. Similarly the wall can be made of wire mesh.

Hence, the tensile force, exerted in the longitudinal direction, forces not only the wall components, which are arranged obliquely to the longitudinal and transverse direction of the structure, but also the wall components, oriented in the transverse direction, to orient themselves more in the longitudinal direction. The transverse orientation of these components decreases, a state that leads to a decrease in the overall circumference and, thus, to a reduction in the diameter of the structure.

One of the two ends of the stent exhibits terminal coupling devices 16, by means of which the end of the stent may be grasped, and the tensile force 15 may be fed into the stent.

In this case the coupling devices are, for example, thickenings, eyes, hooks, plates or the like. They may contain preferably an x-ray opaque material, such as gold, platinum, silver, tantalum, a synthetic plastic material doped with barium sulfate or a synthetic plastic material doped with bismuth trioxide, in order to facilitate the localization of the stent and/or the coupling devices in the x-ray image.

Figure 3:
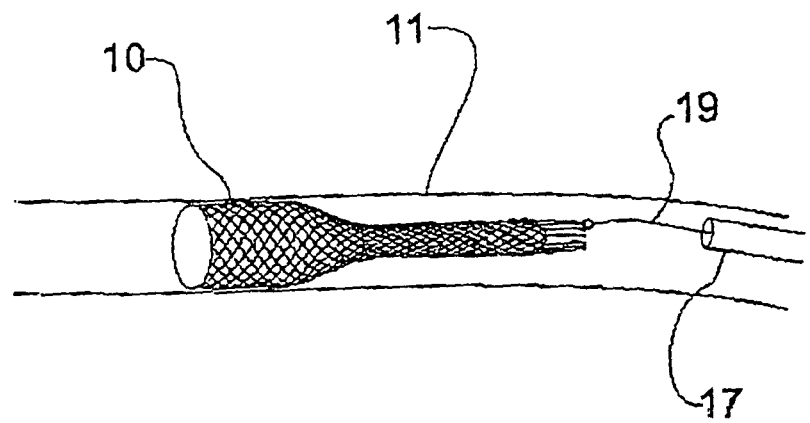
FIG. 3, FIG. 4, and FIG. 5 depict inventive stents that are positioned in a blood vessel and are depicted at the instant, in which they are pulled out again.
Figure 4:
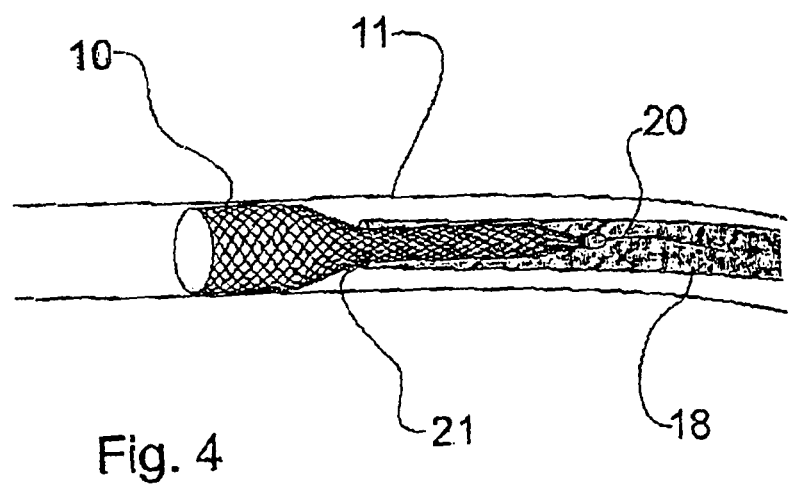

FIG. 3 and FIG. 4 show the stent 10, which is positioned in a blood vessel 11 and which is shown at the instant, at which it is pulled out of said blood vessel.

To this end, a tensile force, acting in the longitudinal direction of the stent, is fed into the stent by means of a catch device 19, 20, which is inserted into the lumen by means of a catheter

17, 18. To this end, an abutment is required, as described above, so that the stent is simply not pulled out of its position in the body lumen.

To this end FIG. 3 shows one possibility, which does not require any additional device-related measures. In this case it is assumed that a stent, which is positioned and expanded in a blood vessel, will adhere to the inner wall of the blood vessel after a while. If at this stage a tensile force is exerted on the stent by means of a catch device 19, the stent will then detach itself from the wall of the blood vessel 11 on the side, from which the force is exerted, but it will continue to adhere to the side that is located further away. This adhesion represents the requisite abutment.

FIG. 4 shows another possibility. In this case the stent is pulled into a catheter 18 having an opening 21—a so-called delivery sheath—by means of a catch device 20. In this case the tensile force, which acts on the stent and which reduces its diameter, is also generated at the instant, at which the stent end abuts the opening of the sheath, which in this case acts as the abutment.

Figure 5:
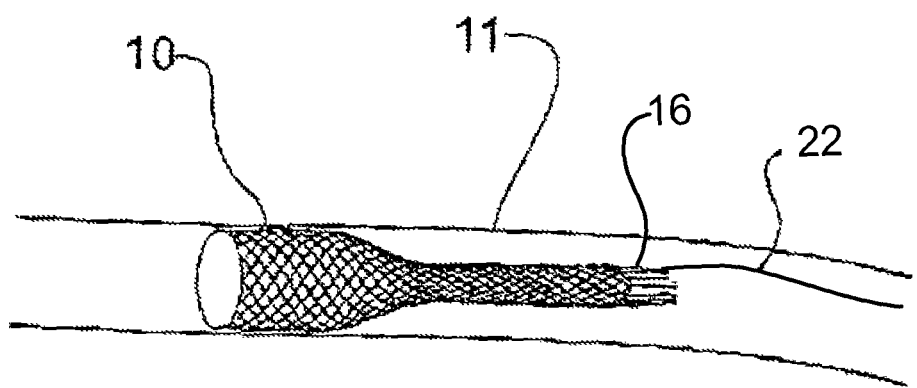

In an alternative embodiment, the end of the stent and/or the coupling device 16 exhibit(s) a wire-like elongation, which runs in accordance with an Ariadne thread along the path of catheterization and projects beyond the body of the patient. For example, as shown in FIG. 5, the end of the stent 10, and more particularly the coupling device 16, exhibits the wire-like elongation 22. In this way it is possible to remove again the temporary stent by just pulling on the end of the wire even without any further catheterization. Owing to the avoidance of another catheterization in order to remove the stent, the stress on the patient and the risk of complications are decreased. It is expedient for the wire-like elongation to grasp at least one coupling element, in particular a plurality and preferably all of the coupling elements 16, as a result of which the coupling elements are connected to each other as well as connected together with the wire by means of connecting elements, which are usually also wire-like or thread-like.

What is claimed is:

1. A medical device comprising:
    a stent to treat a patient, said stent positionable in a body lumen of the patient having an inner lining,
    the stent, in an expanded state, having a cylindrical shape extending along a longitudinal axis formed by a stent wall which defines a diameter of an unobstructed axial passage communicating with open ends at two opposite axial ends of the stent,
    wherein the wall is elastic under tension so that on exertion of a tensile pulling force, acting on one of the ends of the stent in the longitudinal direction, the diameter of the stent decreases over the entire longitudinal extent of the stent; and
    wherein at least one of the ends of the stent exhibits a wire elongation having an end which runs along a path of catheterization and projects beyond the body of the patient; and
    wherein the wall of the stent is made of a woven wire, a knitted wire, and/or a braided wire or a wire mesh; and
    wherein, upon exertion of the tensile pulling force, wall components of the elastic wall of the stent oriented in a direction transverse to the longitudinal axis orient themselves towards the longitudinal axis decreasing the diameter of the stent over the entire longitudinal extent of the stent; and
    wherein the stent is configured such that pulling on said wire end without catheterization allows for retrieval of the stent from the body lumen within a dwell time of two days and wherein said stent is configured to not exert any tangential shear force on said inner lining.

2. The medical device, as claimed in claim 1, wherein at least one of the two ends of the stent exhibits terminal coupling devices, by means of which the end of the stent can be grasped; and the tensile pulling force, acting in the longitudinal direction of the stent, can be fed into the stent.

3. The medical device, as claimed in claim 1, wherein the tensile pulling force, acting in the longitudinal direction of the stent, can be fed into the stent by means of a catch device that is inserted into the lumen by means of a catheter.

4. The medical device, as claimed claim 1, wherein the material of the wall is a material, selected from the group composing stainless steel, a synthetic plastic, nickel-titanium alloy, copper-zinc-aluminum alloy or tungsten.

5. The medical device, as claimed claim 1, wherein the wall material exhibits shape memory properties and/or is biodegradable.

6. The medical device, as claimed claim 1, wherein a surface of the stent is finished, smoothed and/or polished.

7. The medical device, as claimed in claim 1, wherein a surface of the stent is provided with a coating for enhancing slip properties.

8. The medical device, as claimed in claim 1, wherein the stent is configured for application in a blood vessel selected from the group comprising the renal artery, carotis, femoral artery, knee artery, the artery of the lower leg, dialysis shunt or a coronary vessel.

9. The medical device, as claimed in claim 1, further comprising a catheter to position the stent in the body lumen.

* * * * *